(12) United States Patent
Elazhary et al.

(10) Patent No.: US 6,552,004 B1
(45) Date of Patent: Apr. 22, 2003

(54) DELIVERY SYSTEM FOR ENTRAPPING CHARGED MACROMOLECULES AND A METHOD FOR PREPARING SAME

(75) Inventors: Youssef Elazhary, St-Hyacinthe (CA); Boby Makabi-Panzu, Québec (CA); David John Hurley, Brookings, SD (US); Sylvette Laurent, St-Hyacinthe (CA)

(73) Assignee: Universite de Montreal, Montreal (CA)

( * ) Notice: Subject to any disclaimer, the term of this patent is extended or adjusted under 35 U.S.C. 154(b) by 6 days.

(21) Appl. No.: 09/699,890

(22) Filed: Oct. 30, 2000

(51) Int. Cl.$^7$ ................................................ A61K 48/00

(52) U.S. Cl. ...................... 514/44; 435/320.1; 435/455; 514/2; 424/450

(58) Field of Search .............................. 435/320.1, 455; 514/44, 2; 424/450

(56) References Cited

PUBLICATIONS

Wei et al., Biochemistry, vol. 25, pp. 7477–7483, 1986.
Makabi–Panzu et al., Vaccine, vol. 16, No. 16, pp. 1504–1510, 1998.
Luukkonen et al., Virology, vol. 76, pp. 55–59, 1977.
Aurora et al., Biochimica et Biophysica Acta 820, pp. 250–258, 1985.

*Primary Examiner*—Dave T. Nguyen
(74) *Attorney, Agent, or Firm*—Nixon Peabody LLP (57) ABSTRACT

The present invention relates to a new delivery system and method for producing same. The delivery system is a biphasic system of delivering charged macromolecules and comprises a negatively charged hydrophobic organic phase and a positively charged inorganic phase. The organic phase and the inorganic phase entrapping added macromolecules. The macromolecules are entrapped by electrostatic bonds between the organic phase, the inorganic phase and the macromolecules. The method for producing the delivery system comprises the steps of contacting together and mixing a negatively charged organic phase, a charged macromolecule and positively charged inorganic phase.

10 Claims, 11 Drawing Sheets

[Bar chart: % protein entrapment for BSA, Peroxidase, BVDV vaccine — all near 100%]

FIG. 8B

[Bar chart: % bound lipid phase for Handmix, Microfluidiz., Bare system — all near 100%]

_FIG_10A

_FIG_10B

FIG. 11

DELIVERY SYSTEM FOR ENTRAPPING CHARGED MACROMOLECULES AND A METHOD FOR PREPARING SAME

BACKGROUND OF THE INVENTION (a) Field of the Invention

The invention relates to a new delivery system for administering drugs, vaccines or other charged compounds. The present invention also relates to a new method for entrapping charged macromolecules.

(b) Description of Prior Art

In the field of vaccine, there is a growing interest for the development of colloidal delivery systems, similar to liposomes and nanoparticles, but capable of entrapping a fairly large amount of macromolecular proteins. Colloidal delivery systems must also meet the pharmaceutical requirements for product shelf life.

Several colloidal systems have been investigated to develop safer forms of drugs and vaccines. In general, the prime objective of these systems was to allow efficient delivery of pharmaceuticals to a biological site. In this context, macrophages have been identified as being a target for macromolecular proteins delivered by colloidal systems. However, it is well known that efficient delivery of a macromolecular protein to a biological site using colloidal delivery systems requires a stable entrapment of the macromolecular protein in the delivery system used.

According to studies evaluating entrapment of macromolecular protein in delivery systems, the major drawbacks limiting the use in various areas of pharmaceutical industries is a relatively low entrapment capacity of water-soluble macromolecular proteins. Water-soluble macromolecular proteins are poorly entrapped in colloidal systems because of their large size. Usually, the entrapment of large water-soluble macromolecular protein in liposomes depends on the nature of the aqueous phase, and rarely exceeds 50%.

There are several mechanisms suspected to be responsible for the water-soluble protein entrapment in colloidal systems. A general assumption is that water-soluble proteins are freely entrapped in the aqueous phase of the colloidal systems, like liposomes. The entrapment of a much larger water-soluble macromolecular protein is difficult to realize because of their large size. The introduction of giant liposomes and water-in-oil (w/o) emulsions has only partially remedied to the situation, because the efficiency of protein entrapment obtained using these systems does not reflect the actual capacity of the aqueous phase of these systems.

Furthermore, the methods used in the prior art to prepare delivery systems are in general time-consuming and often non-compatible with current pharmaceutical requirements.

As seen above, there is a great need for a delivery system capable of entrapping a broad range in size and a large amount of water-soluble proteins.

SUMMARY OF THE INVENTION

One aim of the present invention is to provide a method for entrapping water-soluble proteins using variable electrostatic interactions.

Another aim of the present invention is to provide a delivery system entrapping water-soluble proteins using variable electrostatic interactions.

Another aim of the present invention is to provide a delivery system prepared by a method already accepted in the pharmaceutical industry.

In accordance with the present invention, there is provided a biphasic delivery system for charged molecules comprising a negatively charged hydrophobic organic phase and a positively charged inorganic phase. The organic phase and the inorganic phase are adapted to entrap charged molecules by electrostatic bonds between the organic phase, the inorganic phase and the at least one charged molecule.

The organic phase is preferably an oil-in-water emulsion, which comprises a neutral oil and a negatively charged organic compound. Such neutral oil is, for example and without being limited thereto, selected from the group consisting of squalane, soybean oil, sesame oil and peanut oil. The negatively charged organic compound is preferably dicetylphosphate.

The inorganic phase of the delivery system of the present invention preferably comprises alum.

The delivery system preferably has a diameter of at most five micrometers when the charged molecules are entrapped therein.

Still in accordance with the present invention, there is provided the delivery system as described above, which further comprises charged molecules. The charged molecules may be for example DNA.

In accordance with the present invention, there is also provided a method for producing a delivery system as defined above. The method comprises the steps of contacting a negatively charged hydrophobic organic phase, charged molecules and a positively charged inorganic phase and mixing same for entrapping the charged molecules between the organic phase and the inorganic phase. Preferably, the negatively charged organic phase and the charged molecules are first mixed together, followed by addition and mixing of the positively charged inorganic phase therein.

The method of the present invention is simple and easily and reproducibly scaled up for industrial applicability. A well-defined and specific size distribution of the delivery system can be prepared with the present method. Hence, the system is another aspect of the present invention, which is meant to include a carrier for macromolecule, an adjuvant for vaccine, a slow-delivery system or a stabilizing agent.

BRIEF DESCRIPTION OF THE DRAWINGS

FIG. 6 illustrates protein entrapment efficiency relative to the organic phase (FIG. 6A) or to the inorganic phase (FIG. 6B), of a preferred delivery system, as a function of protein concentration;

DETAILED DESCRIPTION OF THE INVENTION

Figure 9A:
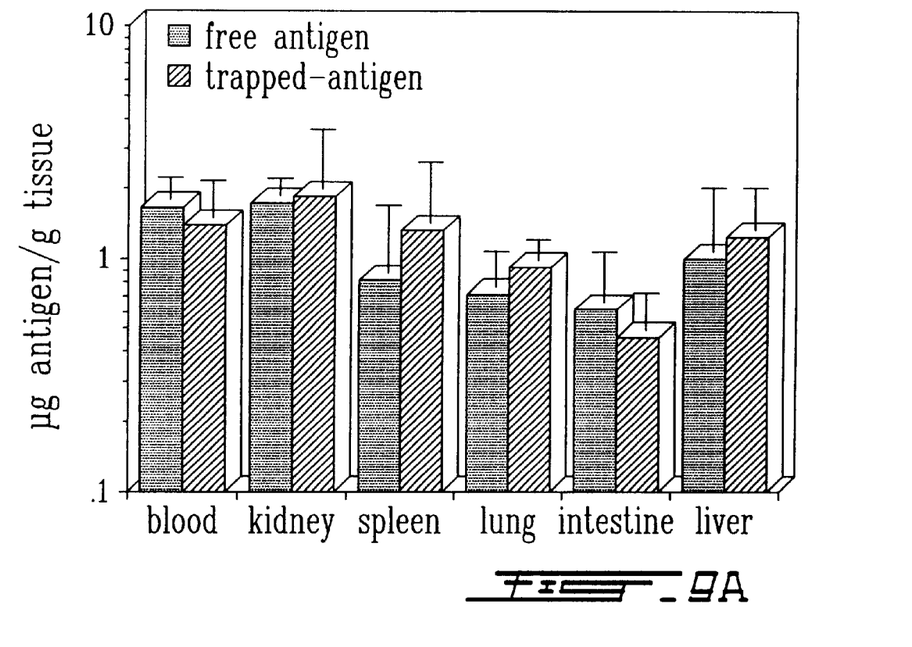
FIGS. 9A and 9B illustrate a comparison of tissue distribution of free and trapped antigen (FIG. 9A) and bare delivery system (FIG. 9B) in Balb/C mice 24 hours after intramuscular injection.
Figure 9B:
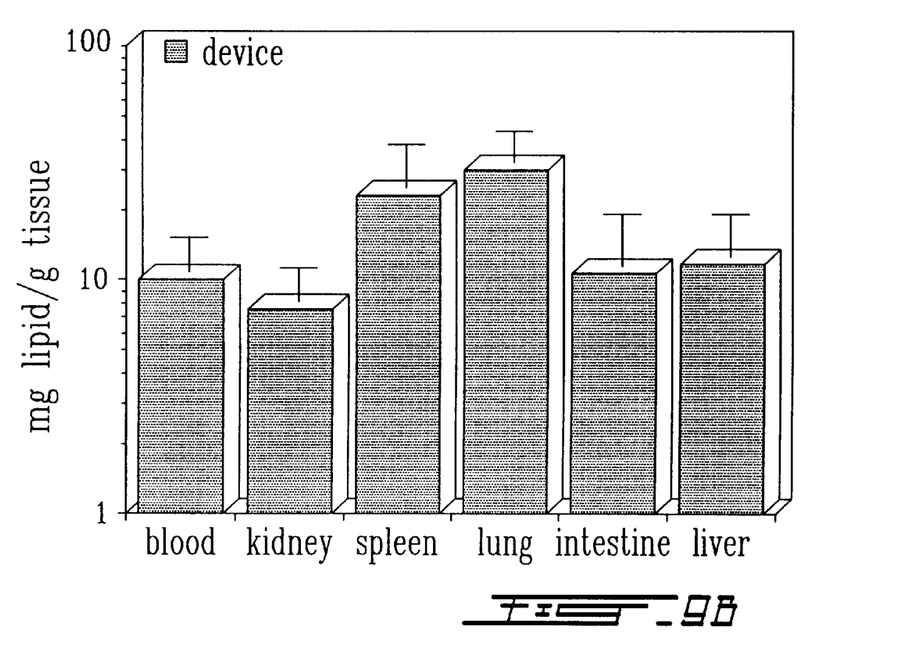
Figure 10A:
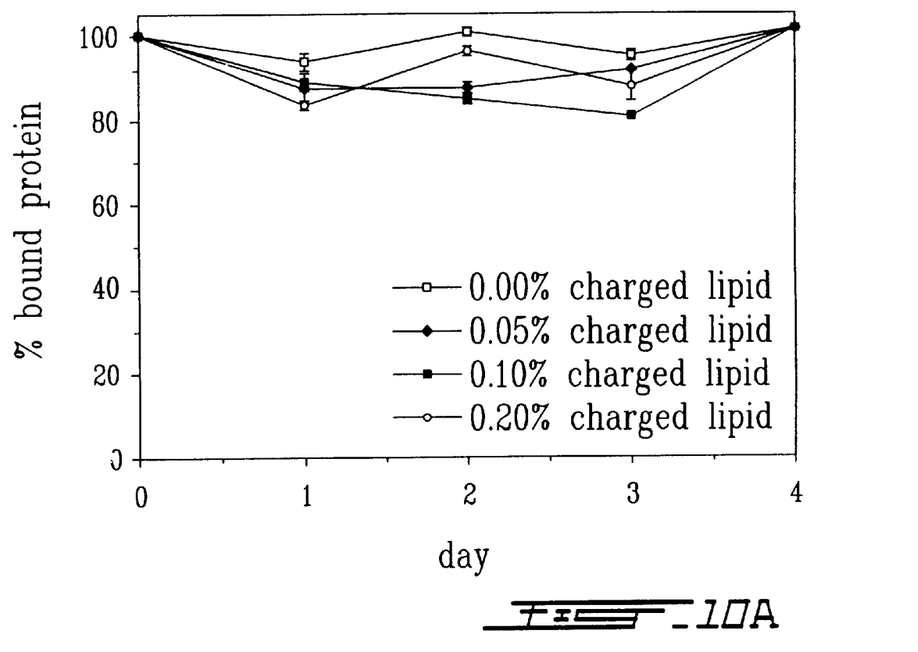
FIGS. 10A and 10B illustrate a time course of a release of an antigen (FIG. 10A) and of the device targeting phase (FIG. 10B) at 37° C. after incubation in medium containing 50% of fetal bovine serum.
Figure 10B:
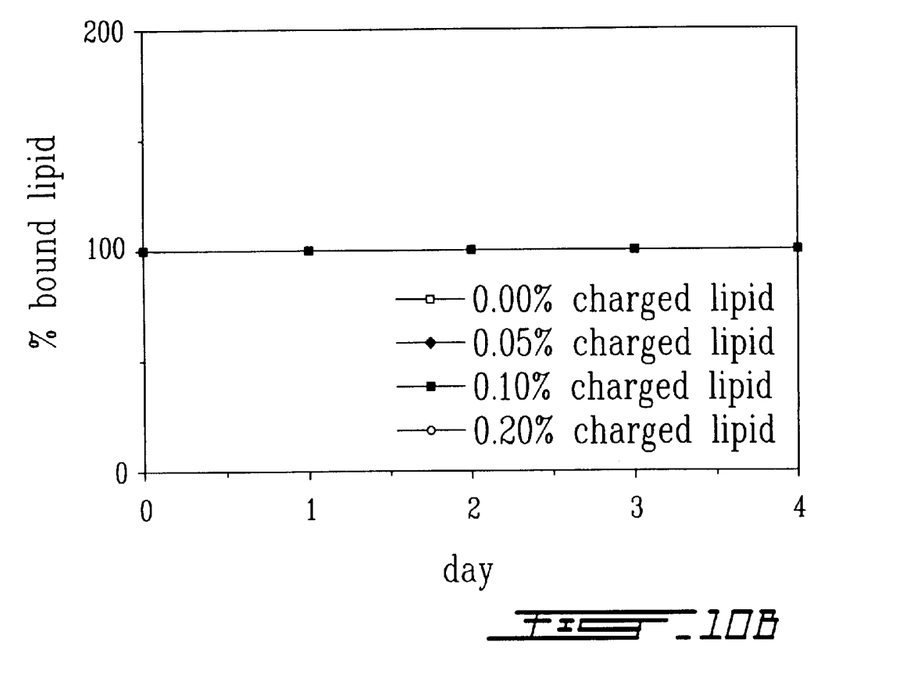

The system of the present invention has a propensity for macrophage-rich tissue of the reticuloendothelial system (RES) in addition to a propensity for accumulating into the lung, intestine and kidney when administered parenterally to animals, as evidenced by the results of tissue distribution illustrated in FIGS. 9A and 9B.

The system is designed to be administered preferably by intramuscular or subcutaneous routes. There have been no problems of toxicity found at the injection site when the delivery system of the present invention was administered.

The delivery system is electrostatically modulable and is capable of entrapping a fairly large amount of protein between its organic and inorganic phases on the sole basis of electrostatic interactions. Moreover, the system can be prepared and sterilized using well-accepted industrial processes in the pharmaceutical industry. For example, the delivery system can be sterilized by filtration or UV irradiation, as well known in the art, and also by autoclaving process (120° C. for 30 minutes), which is believed to be a commercially important property reinforcing its acceptability as a pharmaceutical product.

In accordance with a preferred embodiment of the invention, the delivery system has a better protein entrapping capacity compared to other delivery systems of the prior art. It is composed of a negatively charged hydrophobic emulsion or organic matrix as targeting. phase, and a positively charged inorganic matrix as trapping phase. A preferred positively charged inorganic matrix is mineral alum. The shape, particle average size and size distribution of the emulsion matrix was similar regardless of the oils used for preparing the emulsion matrix. However, squalane, known to be more resistant to lipidic peroxidation occurring during storage, is the most preferred for its high content in saturated fatty acids.

The system of the present invention is readily carried out and has a stable entrapment rate of proteins such as BSA, peroxidase, and inactivated Bovine viral diarrhea virus (BVDV) protein mixture entrapment. Ubiquinone™ 50 was added to the targeting phase of the system of the present invention to increase the hydro-phobicity of the targeting phase, while dicetylphosphate (DCP) was added for conferring to the targeting phase a negative charge given the fact that the trapping phase is positively charged (Makabi-Panzu, B. et al., Vaccine, Vol. 16, No. 16, pp. 1504–1510 (1998)).

As found for liposomes and nanoparticles, the use of a negatively charged hydrophobic colloidal phase has the additional advantage of increasing the macrophage targeting ability of the system by allowing binding of the circulatory serum opsonins. Serum opsonization is known to increase the phagocytosis by macrophages of negatively charged hydrophobic vesicles. Other types of serum proteins have also been tested in the system of the present invention.

Unlike traditional colloidal delivery systems, the delivery system of the present invention comprises a biphasic system containing two oppositely charged phases: a negatively charged organic phase, which is the targeting phase where a protein is to be bound, and a positively charged inorganic phase (trapping phase), in which the negatively charged organic phase is entrapped and caged through variable electrostatic bonds. The protein electrostatically interacts also with the positively charged inorganic phase. The system of the present invention allows for delivery of proteins to the reticulo-endothelial system after administration, preferably intramuscular and/or subcutaneous administration. The system of the present invention allows delivery of the protein bound to the targeting phase and/or to the trapping phase.

Results about physicochemical characterization of the system of the present invention demonstrated that the system is a very stable system displaying a high entrapment capacity for proteins after a year of storage at 4° Celcius in the addition to have the ability of increasing the immunogenicity of vaccines such as BVDV and influenza vaccines. Accordingly, since the system of the present invention has the ability of increasing the immunogenicity of vaccines, there is therefore no need or a lesser need for boosters. A vaccine which required 2 boost for being efficient, when prepared in accordance with the present invention, may now only require one boost, or no boost at all, depending of the protein to be immunized against, and the overall immunogenicity of the protein entrapped in the delivery system of the present invention.

RADIO LABELING OF BVDV AND CELL GLYCOPROTEIN MIXTURE

The Bovine viral diarrhea virus (BVDV) and cell surface glycoproteins are used herein as an example of large water-soluble proteins to be entrapped in the system of the present invention. The BVDV surface glycoproteins have been labeled according to a galactose oxidase-[$^3$H]borohydride procedure (Lukkonen, A. et al., Virology, 76:55 (1977)) using a Pellet of virus-containing cell culture supernatant precleared by centrifugation (25000 g, 3 h at 4° C.). Briefly, the virus Pellet preparation, treated with 0.5% triton™ X-100 solution for one hour before being suspended in PBS, was first incubated with galactose oxidase for 60 minutes at 37° C. and thereafter with 500 $\mu$Ci of sodium boro[$^3$H] hydride for 30 minutes at room temperature. Labeled viruses were separated using Sephadex 50™ columns after a low centrifugation (200 g, 15 minutes at 4° C.). Finally, labeled glycoproteins were pooled and stored at −70° C.

PREPARATION OF THE DELIVERY SYSTEM

In accordance with a preferred embodiment of the present invention, the delivery system was prepared by contacting 140 mg of a commercially available alum pellet with 2 ml (32.4 mg) of neutral oil-made oil-in-water emulsion as follows. One hundred (100) ml of emulsion was prepared by microfluidization (12,000 psi, 3 cycles or 20,000 psi, one cycle, at room temperature) in PBS Ubiquinone™ 50, 4 ml of a neutral oil (Squalane, soybean oil, sesame oil, or peanut oil), 100 mg of dicetylphosphate and 2 ml of Tween™ 80:span 85 (1:1, v/v) mixture. Vitamins may optionally be added to this solution. A volume of the freshly prepared emulsion is then added to an equal volume of protein solution in PBS before being reacted with alum. The amount of alum used to prepare the system was determined as being the amount necessary to bind 100% of the amount of emulsion preparation added. To determine the amount of alum, 2 ml (32.4 mg) of the tritiated oil emulsion is reacted with different amounts of alum. Residual radioactivity in the supernatant was monitored after a low centrifugation (200 g, 15 minutes) at 4° C. The preferred amount of alum is the one for which radioactivity in the supernatant is minimal.

In a preferred embodiment of the present invention, the amount of dicetylphosphate used can be varied for modulating electrostatic interactions between a macromolecule and the delivery system to vary the release rate of the macromolecule by the system. Creating strong electrostatic interactions by adding more dicetylphosphate can eventually slow down the delivery rate of the system up to a slow-released delivery system. In that, the release rate of the system of the present invention is thus variable.

The delivery system can be prepared with or without the antigen, in which case the antigen is added at a later time.

PARTICLE SIZE DISTRIBUTION AND SHAPE ANALYSIS

Particle size and shape measurements were performed by photon correlation spectroscopy and transmission electron microscopy after sample negative staining with a 1% uranyle acetate aqueous solution as outlined by Aurora et al. (*Biochim. Biophys. Acta*, Vol. 820, pp. 250–258 (1985); Wei, L. and Thomas, H.LH., *Biochemistry* Vol. 25, pp. 7477–7483 (1986)). The results of size measurement are quoted as particle average size and size distribution. Electron microscopy pictures with appropriate magnification allowed visualization of the system shape (FIGS. 3A, 3B, 5A and 5B).

MACROMOLECULE ENTRAPMENT

The BVDV surface glycoprotein entrapment in the delivery system was determined either after microfluidizing once, at 12 000 psi and room temperature, equal volumes of a well-defined size emulsion and macromolecule solution before preparing the system of the present invention, or, after microfluidizing together, under similar conditions, equal volumes of already mounted system suspension and protein solution (50 ml of protein solution plus 50 ml of mounted system). In both cases, the amount of entrapped protein in the device was determined by monitoring, using a commercially available bucinchoninic acid (BCA) protein assay, sold by Pierce. The presence of the protein in the supernatant, in comparison to the total amount of protein added, was also determined after extraction with methanol:chloroform (1:2).

PROTEIN DETERMINATION

Protein concentrations in the present system have been determined using commercially available BCA assay with BSA as standard.

TISSUE DISTRIBUTION STUDIES

The in vivo experiments were done with female Balb/C mice weighing 17 to 20 g, as reported in Makabi-Panzu, B. et al., *Vaccine*, Vol. 16, No. 16, pp. 1504–1510 (1998). The delivery system of the present invention was administered intramuscularly to mice distributed in groups of 6, at a dose of 1,000,000 DPM per mouse. In most cases, the specific activity of the injected system was 1 µCi per mg of neutral oil using a non-exchangeable and non-metabolizable tritiated hexadecyl-ether-cholesterol as marker of the device targeting phase. The tissue distribution was determined 24 hours after administration of the labeled whole device to mice. The following tissues were taken: lung, spleen, liver, intestine, kidney and plasma. Samples were weighed and disrupted with a tissue blender (model 985-370, Xymotech Biosystems) in a minimal volume of 0.25% Triton X-100™ solution (20 mg of tissue per ml). Aliquots of 200 µl or 300 µl of the homogenates were digested for 3 hours at 60° C. with Beckman tissue solubilizer 450 (Beckman Canada Inc., Mississauga, Ontario). An appropriate volume of 30% hydrogen peroxide was then added to discolor the sample before scintillation counting in order to avoid quenching (50 µl per ml of tissue homogenate or add another 50 µl if no discolored). After 18 hours at room temperature in tightly closed vials, 70 µl of glacial acetic acid were added to the samples to avoid chemiluminescence. An appropriate amount of scintillation cocktail such as Ecolite™ (from Amersham Canada) was added to the samples which were then counted in a liquid scintillation counter (liquid scintillation counter, LKB Wallac, 1217 Rackbeta, Turku, Finland). The distribution of the system in the mice was evaluated from the radioactivity (DPM counts) per total tissue weight and converted to mg of injected system per g of tissue.

RESULTS

PREPARATION OF THE DELIVERY SYSTEM

Figure 1:
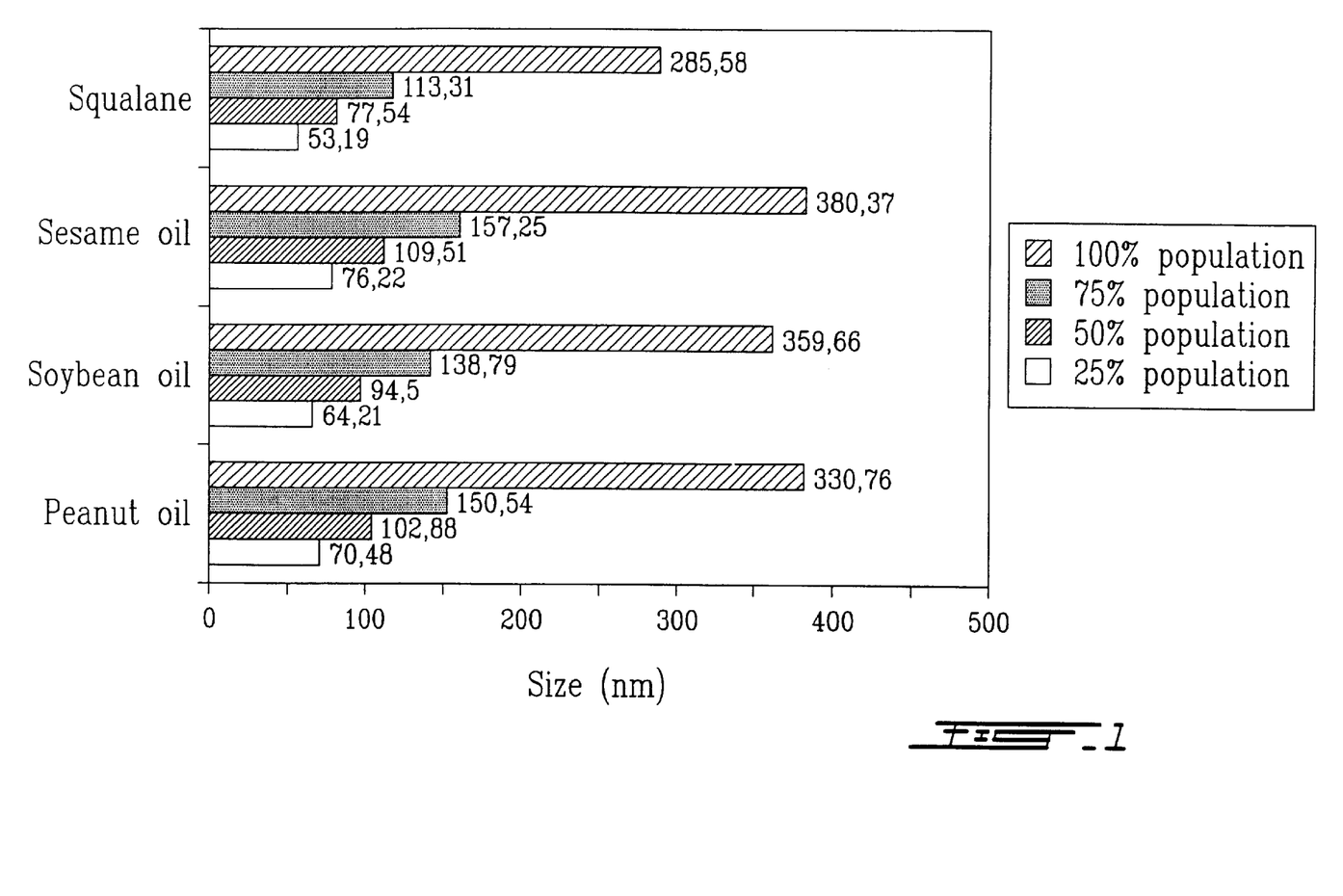
FIG. 1 illustrates results of tests of various electrostatically neutral oils for the preparation of the targeting organic phase of the delivery system in accordance with a preferred embodiment of the present invention.
Figure 2:
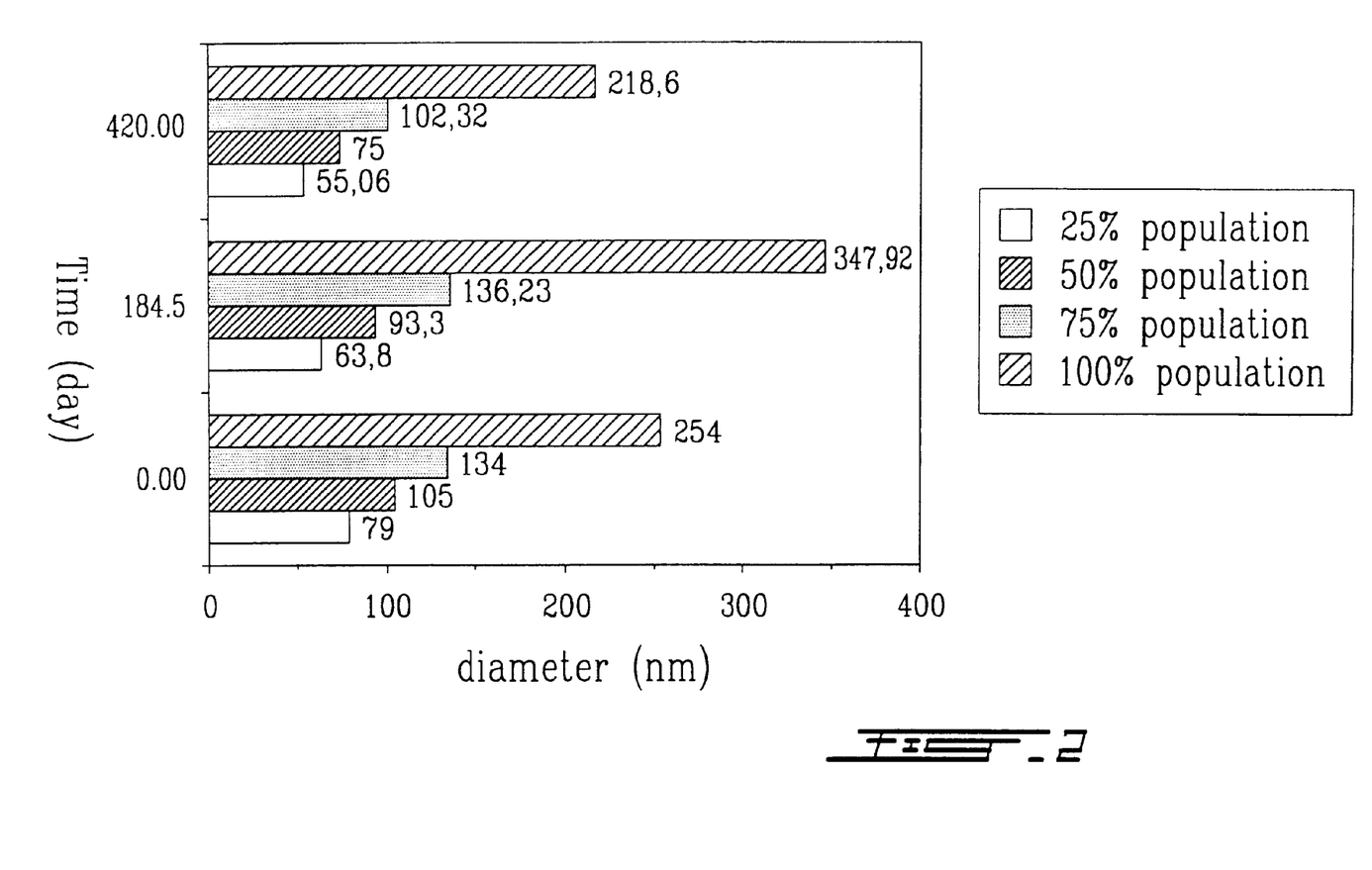
FIG. 2 illustrates droplet size distribution of a squalane emulsion targeting phase of the delivery system in accordance with a preferred embodiment of the present invention, 420 days after storage at 4° C.
Figure 3A:
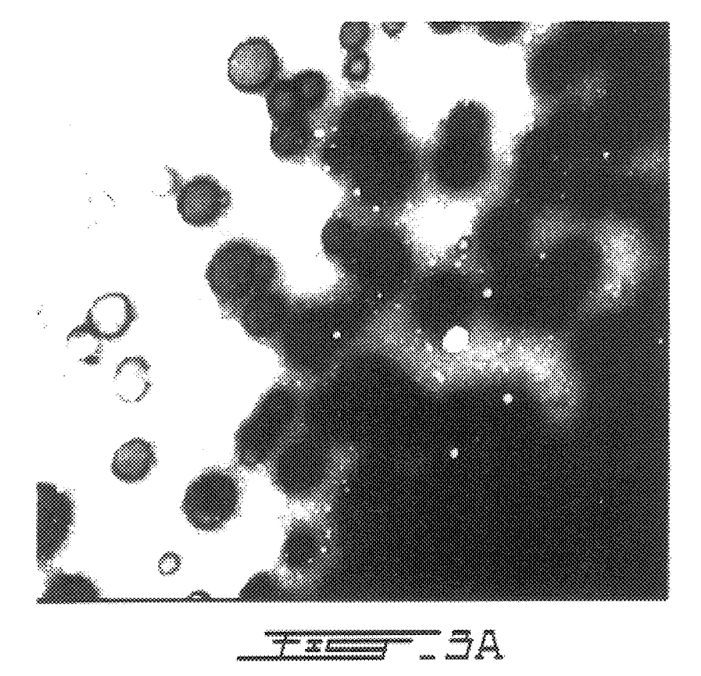
FIGS. 3A and 3B illustrate electronic micrographs showing droplet shape and size distribution of the organic phase at a magnification of 10.5K (FIG. 3A) and 51K (FIG. 3B)
Figure 3B:
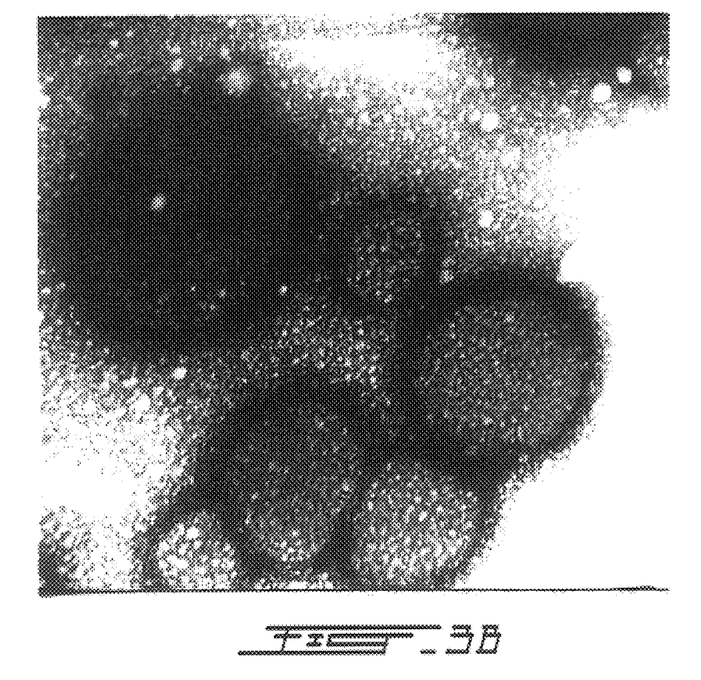

The delivery system was constructed by contacting together a negatively charged emulsion-based organic phase with a positively charged alum-based inorganic phase. Four preferred neutral oils, namely soybean oil, sesame oil, peanut oil, and squalane, have been tested to form the organic phase of the delivery system in form of submicronic oil-in-water emulsions. In general, no difference in terms of shape, particle average size, and particle size distribution was found (FIGS. 1 and 3). All emulsions prepared consisted mostly of globular droplets of less than 400 nm of diameter, similarly distributed. Squalane was chosen for further studies because of its high content in saturated fatty acids. Squalane emulsions displayed a very good long term colloidal stability after over 420 days of storage at 4° C. (See FIG. 2). By contrast, the alum used to prepare the inorganic phase of the delivery system of the present invention is a ready-to-use commercial preparation. (Sold by Accurate Chemical, Westbury, N.Y., USA).

Figure 4:
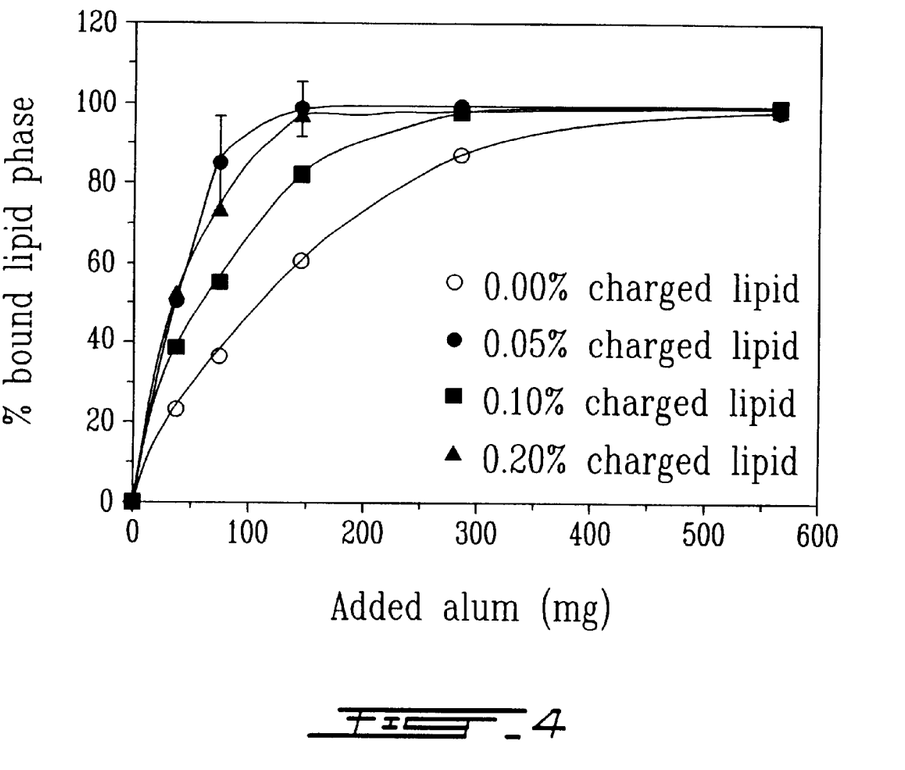
FIG. 4 illustrates a graph used for evaluating the amount of alum used in the trapping phase of a preferred embodiment of the delivery system of the present invention.

In FIG. 4, 140 mg of this alum was found suitable to mount the whole delivery system. This alum amount is the amount which totally binds the amount of organic phase used (32.4 mg). FIG. 4 illustrates the amount of alum necessary for binding the organic phase of the delivery system of the present invention. As can be seen in FIG. 4, a plateau is reached when more than 140 mg of alum is used. The amount of alum used was that caging a maximum amount of the lipid phase. This maximum amount has been determined by interacting different amounts of alum with 2 ml of tritiated lipid phase at room temperature.

PROTEIN ENTRAPMENT EFFICIENCY OF THE DELIVERY SYSTEM

Figure 5A:
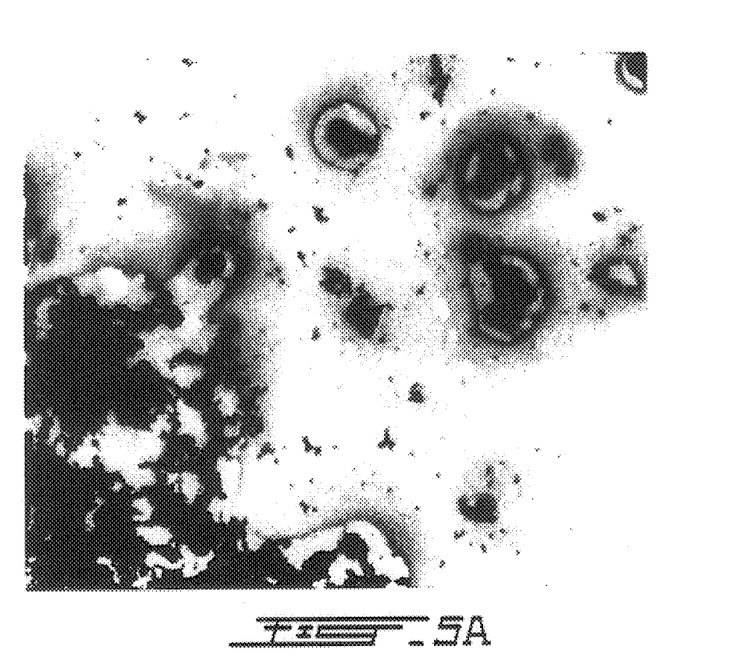
FIGS. 5A–B illustrate electronic micrographs of a delivery system in accordance with one embodiment of the present invention at a magnification of 3.3K (FIG. 5A) and 51K (FIG. 5B)
Figure 5B:
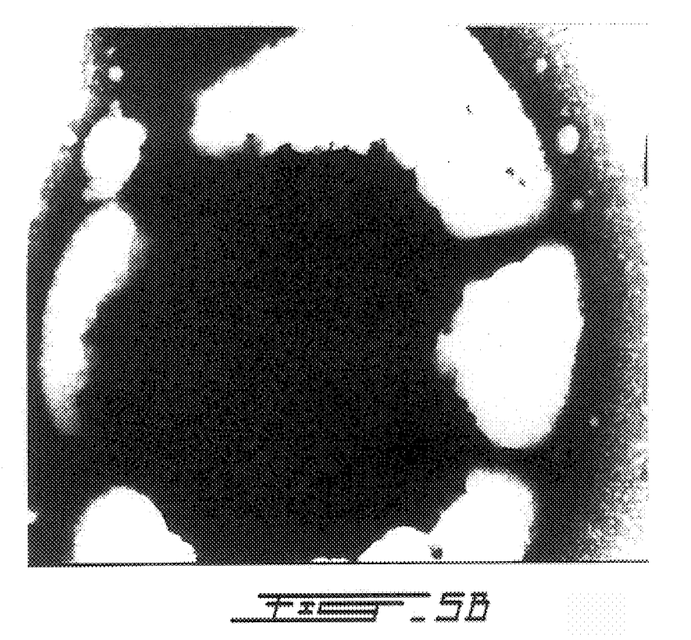
Figure 6A:
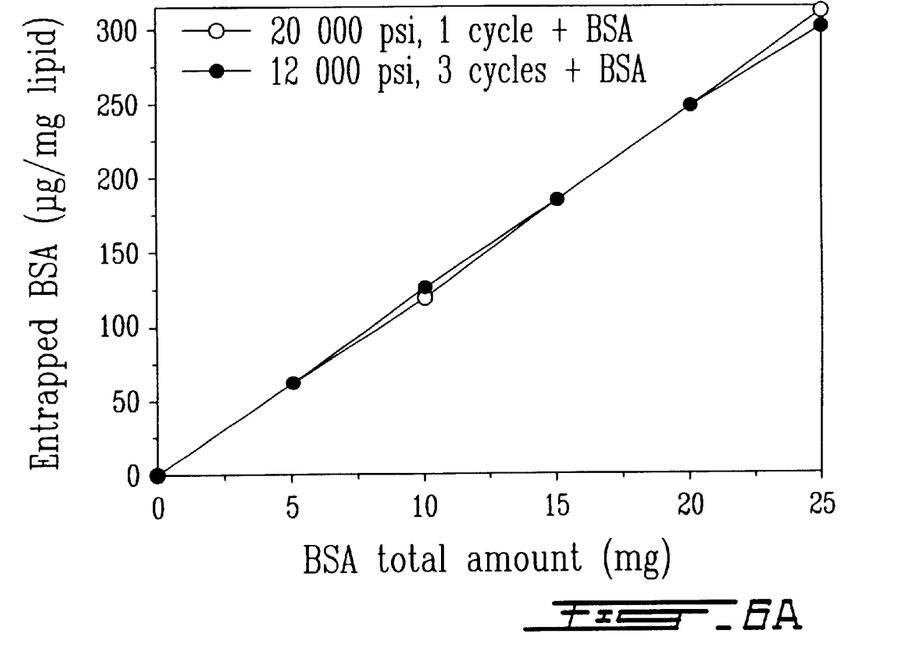
Figure 6B:
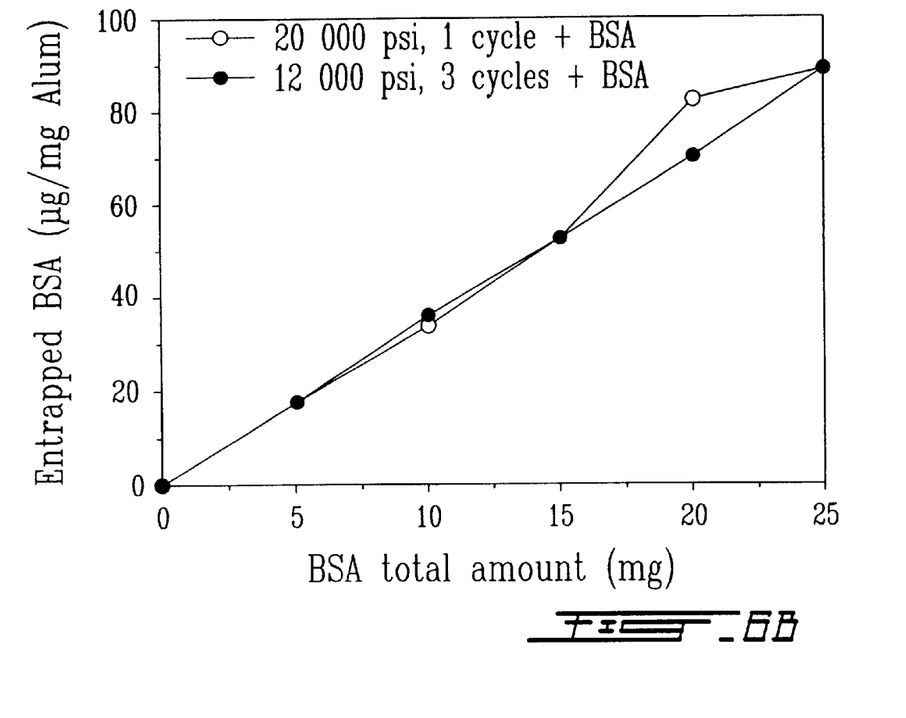
Figure 7:
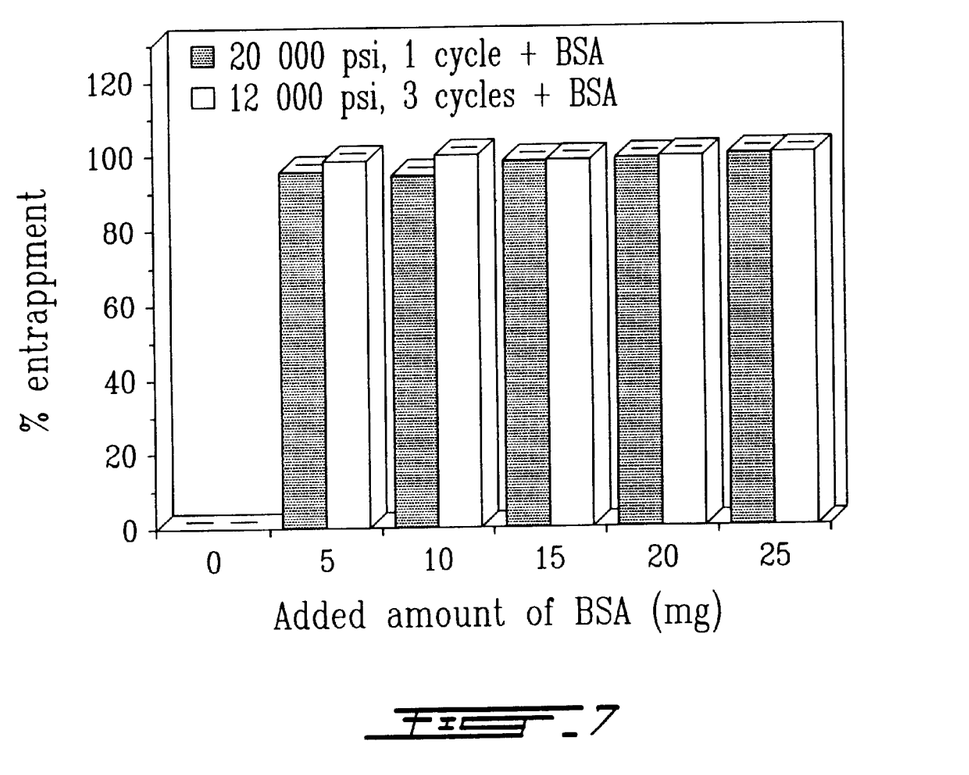
FIG. 7 illustrates the percentage of entrapment capacity of a preferred embodiment of the delivery system of the present invention, relative to the concentration of protein added.
Figure 8A:
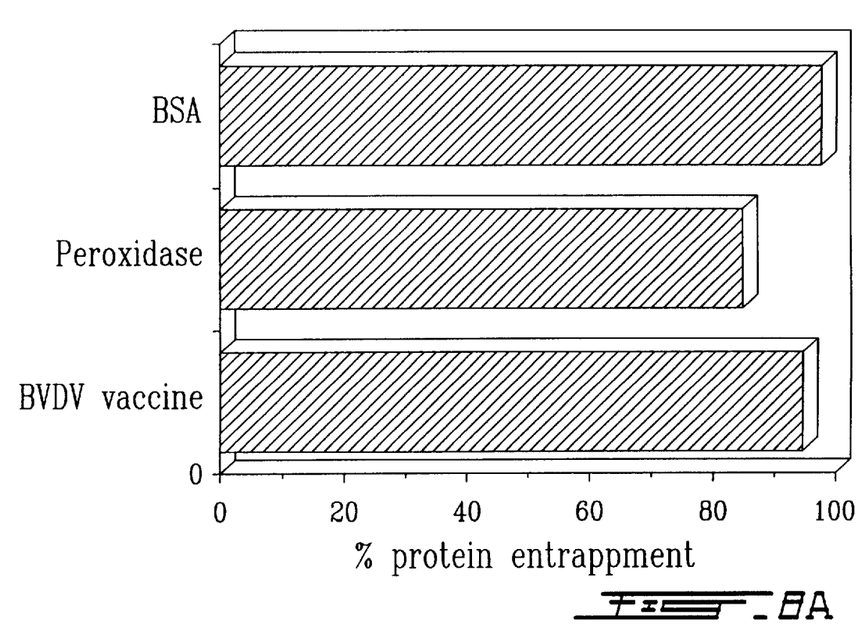
FIGS. 8A and 8B illustrate the entrapment ability of a preferred embodiment of the delivery system of the present invention for various protein types (FIG. 8A) and a comparison of microfluidization and hand-mix entrapment strategies (FIG. 8B)
Figure 8B:
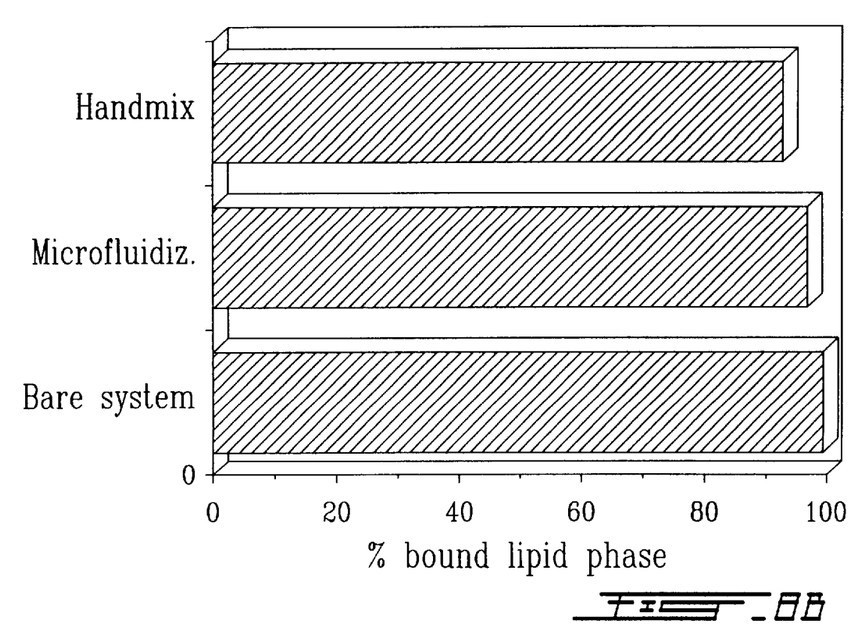

The delivery system of the invention displayed a very good capacity for entrapping proteins as shown in FIGS. 5 and 6. The protein entrapment capacity of the system of the present invention, evaluated using various amounts of bovine serum albumin (BSA) as model, exceeded 25 mg when Ubiquinone 50 was not used in the formulation. The percentage of entrapment of BSA under the same conditions was about 90 to 100%, independently of the preparation strategy used, and/or the amount of lipid in the emulsion phase. A high correlation is seen between the lipid content of the emulsion phase and the entrapment protein efficiency of the system (Table 1, FIG. 7). The delivery system displayed similar entrapment behavior using other proteins and/or a handmixing entrapment method (See FIG. 8).

TABLE 1

Effect of strategy of microfluidization on protein entrapment in the delivery system and influence of the amount of the colloidal lipidic (targeting phase) and alum phases (trapping phase)

| Entrapement strategy | Microfluidizing conditions | lipid μg/mg SD* | Alum μg/mg | % entrapment |
|---|---|---|---|---|
| Entrapment after emulsion preparation | 12000 psi, 3 cycles plus protein | 244.50 ± 1.06<br>120.84 ± 0.93 | 69.86 ± .03<br>40.28 ± .03 | 97.80 ± 0.42<br>96.70 ± 0.74 |
|  | 20000 psi, 1 cycle plus protein | 244.25 ± 1.77<br>121.50 ± 0.88 | 69.79 ± 0.50<br>40.50 ± 0.29 | 97.20 ± 0.71<br>97.20 ± 0.71 |
| Entrapment during emulsion preparation | 12000 psi, 2 cycles minus protein and 1 cycle plus protein | 244.75 ± 1.06<br>120.37 ± 1.06 | 69.93 ± 0.30<br>40.12 ± 0.02 | 97.9 ± 0.42<br>96.30 ± 0.42 |
|  | 20000 psi, 1 cycle minus protein and 12000 psi, 1 cycle plus protein | 244.12 ± 1.77<br>121.50 ± 0.88 | 69.75 ± 0.05<br>40.50 ± 0.29 | 97.70 ± 0.07<br>97.20 ± 0.07 |

*represents mean value (standard deviation)

IN VIVO DISPOSITION OF THE DELIVERY SYSTEM IN THE BODY

As reported in FIG. 9, the targeting phase of the delivery system of the present invention, when administered intramuscularly to BALB/C mice, preferentially accumulated in the macrophage-rich tissue of the RES at 24 hours postinjection. Significant accumulation of the system was also observed in tissues such as intestine, kidney and in the circulation.

It has been shown that the delivery system of the present invention can be used as a vehicle or carrier to deliver charged proteins preferably intramuscularly or subcutaneously. Macromolecules are entrapped based on their charge and electrostatic interaction with the delivery system. Electrostatic charges of the system can be varied to modulate the interaction between the delivery system and the macromolecule to be entrapped, and thus modulate the macromolecule release response of the system. To the opposite to the systems of the prior art, the delivery system not only targets macrophage, but also targets tissues such as lung, spleen, liver, intestine, kidney and plasma.

The present invention will be more readily understood by referring to the following example, which is given to illustrate the invention rather than to limit its scope.

EXAMPLE I

Labeling of BVDV-infected MDBK Glycoproteins by Galactase Oxidase Tritiated Borohydride Procedure Virus-containing cell culture supernatant is precleared by centrifugation at 25,000 g for 3 hours at 4° C. The pellet containing glycoproteins is resuspended in PBS and treated with an equal volume of a 0.5% triton X-100™ solution for one hour at 4° C. Twenty five (25) units of galactose oxidase is then added and incubated for one hour. Tritiated sodium borohydride (500 μCi) is then added and incubated at room temperature for 30 min. Free label (radioisotope) is removed using a Sephadex™ G50 column after a low speed centrifugation at 200 g for 15 minutes at 4° C. The glycoproteins so-labelled are pooled and stored at −70° C. until use.

EXAMPLE II

Preparation and Characterization of the Delivery System of the Present Invention Preparation The system has been prepared by microfluidizing in a volume of 100 ml at 12 000 psi 4 ml of squalane, 1 ml of span 85, 1 ml of tween 80, 100 mg of ubiquinone 50 (U50), 100 mg of dicetylphosphate (DCP), 20 mg of vitamin A and 100 mg vitamin E as follow: briefly, appropriate volumes of U50, DCP, vitamins A and E dissolved in methanol:chloroform (2:1) were added in a 100-ml bottle, and the solvent organic was evaporated using nitrogen gas stream before adding appropriate amounts of squalane, span 85 and tween 80. The mixture was then microfluidized three times in 100 ml of PBS. The obtained emulsion was finally sterilized by autoclaving at 120 degrees for 15 min. At the end of the autoclaving process, separated U50 phase was readhered by simply agitation of the bottle once its temperature was cooled down enough to be handled by hands. Usually, 14 ml of emulsion phase was contacted with 980 mg of Alum to form a gel like mixture at room temperature. The macromolecule was entrapped by simply mixing with an equal volume of prepared adjuvant system (also referred to herein as delivery system) suspension. This procedure is called preformed procedure using preformed adjuvant system emulsion phase or premounted delivery system suspension. An alternative procedure consisting in the entrapment of the macromolecule during the microfluidization step is called stepwise procedure.

Particle Size

The particle size of delivery system emulsion phase was analyzed using a nanosizer (coulter) which is suited for measuring particles of less than 1 μm where resolution is greatest although large particles can also be quantitated with less precision.

Macromolecule Entrapment

In order to characterize the partition of free and bound macromolecule in the adjuvant system, the macromolecule entrapment efficiency of the system was evaluated. Free macromolecules were separated from bound macromolecules by low centrifugation (13 000 rpm, 15 min, at room temperature), and the amount of entrapped macromolecule was evaluated in comparison to the initially added amount of macromolecule using a BCA protein assay in the case of protein or simply evaluating at UV wavelength (260 nm) in the case of DNA measurement.

Release of Bound Macromolecule From the Adjuvant System

The measurement of the release of macromolecule from the adjuvant system gives a good idea about the capacity of the system to differentially modulate the immune responses through bound macromolecule by mostly targeting APCs such as macrophages. 1 ml aliquots of adjuvant system containing bound macromolecule was incubated at 4, 25, 37 and 60° C. in PBS. The release of macromolecule was monitored in supernatant at different periods of time. The amount of released macromolecule was evaluated in the supernatant after extraction with equal volume of methanol/chloroform (½) using a BCA protein assay in the case of proteins or by simply measuring at 260 nm in the case of DNA.

Stability Evaluations

The stability of the adjuvant system was also evaluated by monitoring by naked eyes the creaming process, phase separation, and aggregation of the preparation after a 2 years of storage at 4° C.

Results and Discussion

Table 2 shows the formulation of the emulsion phase of the delivery system of the present invention. As can be seen from this table, the emulsion is made of negatively charged squalane because of the presence of dicetylphosphate. The squalane serves as matrix to other ingredients such as ubiquinone 50, vitamins A and E. Ten (10) ml of 10% solution of ubiquinone 50, dicetylphosphate, vitamins E and 10 ml of 2% solution of vitamin A were used to prepare the emulsion phase.

TABLE 2

Formulation

| Composition | Content (%) |
| --- | --- |
| Squalane | 4.00 (v/v) |
| Tween 80 | 1.00 (v/v) |
| Span 85 | 1.00 (v/v) |
| Ubiquinone 50 | 0.10 (v/w) |
| Dicetylphosphate | 0.10 (v/w) |
| Vitamin E | 0.10 (w/v) |
| Vitamin A | 0.02 (v/w) |

The squalane matrix is made of stable 200 nm droplets suspended in an aqueous PBS solution. The droplets were resistant to the autoclaving process because their size was not much affected by the high temperature during the autoclaving process (121° C., 15 min) (see Table 3). In Table 3, the size of droplets of emulsion stored at 4 degrees was determined using a Coulter nanosizer at 2 years and 5 days post preparation.

TABLE 3

Particle size of the adjuvant system emulsion phase

| Emulsion age | Autoclaving Before | treatment After |
| --- | --- | --- |
| 2 year old | ND | 540 nm ± 59 |
| 5 day old | 189 nm* ± 59 | 146 nm ± 74 |

*represents mean ± SD,
n = 3.

In Table 4, the stability of the emulsion phase was monitored in the presence of BSA interacting with the droplet depending of the strategy of preparation used. Stepwise strategy consisted in the entrapment of the protein during the preparation of emulsion of the preformed strategy consisted in the entrapment of the protein using preformed droplets.

TABLE 4

Stability of the emulsion adjuvant system after 2 years of storage at 4 degrees - Influence of protein presence

| Pressure | Preparation strategy | Aggregation |
| --- | --- | --- |
| 12 000 psi | Stepwise | + (>10 mg/ml) |
| 12 000 psi | Preformed | + (>20 mg/ml) |
| 20 000 psi | Stepwise | + (>10 mg/ml) |
| 20 000 psi | Preformed | + (>20 mg/ml) |

Although autoclaving process provoked separation of ubiquinone 50 which was re-adhered on oily droplets by a simple shaking of the bottle at a temperature around 40–50 degrees, the reaction with alum phase produced a quite stable system with a high capacity of protein entrapment even after 2 years of storage at 4° C. (Tables 5 and 6). The capacity of entrapment of the 2 year old system was comparable to that of the freshly prepared system (Table 5).

TABLE 5

Protein binding capacity of the adjuvant system after 2 years of storage - Comparison with Alum protein capacity

| BSA (mg) | Adjuvant system % | Alum % |
| --- | --- | --- |
| 00.00 | 000 + 0.00* | 000 + 0.00 |
| 03.12 | 100 + 0.18 | 093 + 1.50 |
| 06.25 | 100 + 0.17 | 088 + 2.71 |
| 12.50 | 090 + 0.15 | 079 + 1.97 |
| 19.00 | 065 + 0.45 | nd |
| 25.00 | 049 + 1.95 | 065 + 4.40 |

*represents mean value ± SD,
n = 3.
nd means nondetermined.

The percentage described in Table 5 are calculated from the amount of protein remaining entrapped with respect to the amount originally used.

Protein binding capacity is defined as the amount of initially added protein totally taken up by the system. Different amounts of proteins were mixed with system aliquots and the entrapped protein was evaluated by comparing the amount of protein in the supernatant to that initially added using a BCA protein assay after extraction with equal volume of methanol/chloroform.

The 2-year-old system displayed an entrapment capacity higher than that of alum (Table 6).

TABLE 6

Comparison of protein binding capacities of freshly prepared and 2 year old adjuvant systems

| BSA (mg) | New preparation % | Old preparation % |
| --- | --- | --- |
| 00.00 | 000 + 0.00* | 000 + 0.00 |
| 03.12 | 100 + 0.43 | 100 + 2.60 |
| 06.25 | 100 + 0.07 | 100 + 0.17 |
| 12.50 | 095 + 0.67 | 094 + 0.69 |
| 25.00 | 047 + 2.04 | 039 + 4.10 |

*represents mean value ± SD,
n = 3.

The percentage used in Table 6 are calculated from the amount of protein entrapped with respect to the amount of protein originally used.

In addition to entrap a negatively charged protein, the system retained also a significant amount of a positively charged protein (Table 7).

TABLE 7

Entrapment capacities of adjuvant system for positively and negatively charged macromolecules

| Protein (mg) | BSA (negative) % | Spermidine (Positive) % |
|---|---|---|
| 00.00 | 000 + 0.00 | 000 + 0.00* |
| 03.12 | 100 + 0.43 | 100 + 0.00 |
| 06.25 | 100 + 0.07 | 056 + 8.14 |
| 12.50 | 095 + 0.67 | 042 + 4.43 |
| 25.00 | 047 + 2.04 | 017 + 4.44 |

*represents mean value ± SD,
n = 3.

The percentage represented in Table 7 are calculated from the amount of protein entrapped in the system with respect to the amount of protein originally used.

The delivery system of the present invention was able to entrap a quite great amount of influenza vaccine at high concentration (Table 8).

TABLE 8

Influenza vaccine partition in the adjuvant system

| Sample | Free antigen % | Bound antigen % | Total % |
|---|---|---|---|
| 2 year old prep. | 014 + 0.27* | 086 + 0.27 | 100 + 0.00 |
| 5 day old prep. | 016 + 2.56 | 084 + 2.56 | 100 + 0.00 |
| Antigen solution | 100 + 2.20 | 000 + 0.00 | 100 + 0.00 |
| Bare system | 000 + 0.00 | 000 + 0.00 | 0.00 + 0.00 |

*represents mean value ± SD,
n = 3.

An Influenza vaccine solution containing 1.25 mg of total protein as evaluated with the use of a BCA protein assay was tested here. The entrapped protein was determined as described in the table 5.

The results of protein release from the system after incubation in PBS at different temperatures (4, 25, 37 and 60° C.) for three weeks confirmed the stability of the system in term of entrapping a protein such as BSA (Table 9).

TABLE 9

Protein entrapment stability (%) of the system after three days of incubation at different temperatures

| | Temperature | | | |
|---|---|---|---|---|
| Sample | 4° C. | 25° C. | 37° C. | 60° C. |
| 2 years old prep. | 100 ± 0.00* | 100 ± 0.00* | 100 ± 0.00 | 100 ± 0.00 |
| 5 days old prep. | 100 ± 0.00 | 100 + 0.00 | 100 ± 0.00 | 100 ± 0.00 |

*represents mean value ± SD,
n = 3

In table 9, aliquots of adjuvant system entrapping 12.5 mg of protein were incubated at indicated temperatures for three days and protein released in the supernatant was evaluated as described above using a BCA protein assay.

The stability is expressed as a percentage of remaining bound protein with respect to initial bound protein.

A stable entrapment of protein was found after three days and one, two and three weeks for all incubation temperatures used (Tables 9 to 12). The entrapment capacity of the adjuvant system seemed to irreversibly increase with the incubation temperature in the presence of an excess amount of protein (Tables 10 to 12) because no protein release was observed from the samples after a long period of storage (three weeks) at 4° C. The adjuvant system also displayed a higher entrapment capacity for DNA in addition to entrap a large amount of protein.

TABLE 10

Protein entrapment stability of the system after one week of incubation at different temperatures

| Protein (mg) | Temperature | | | |
|---|---|---|---|---|
| | 4° C. | 25° C. | 37° C. | 60° C. |
| 00.00 | 00.00 ± 0.00 | 00.00 ± 0.00 | 00.00 ± 0.00 | 00.00 ± 0.00 |
| 03.12 | 100.00 ± 0.03 | 99.00 ± 0.74 | 99.00 ± 0.20 | 100.00 ± 0.05 |
| 06.25 | 100.00 ± 0.06 | 100.00 ± 0.11 | 99.00 ± 0.44 | 100.00 ± 0.06* |
| 12.50 | 100.00 ± 0.05 | 100.00 ± 0.02 | 100.00 ± 0.03 | 99.00 ± 0.06 |
| 25.00 | 59.00 ± 1.14 | 63.00 ± 1.50 | 75.00 ± 0.05 | 88.00 ± 0.09 |

*represents mean value ± SD, n = 3

The assay represented in Table 10 was conducted similarly as the one represented in Table 9, except that aliquots of adjuvant system mixed with different amount of BSA have been used.

TABLE 11

Protein entrapment stability of the system after two weeks of incubation at different temperatures

| Protein (mg) | Temperature | | | |
|---|---|---|---|---|
| | 4° C. | 25° C. | 37° C. | 60° C. |
| 00.00 | 00.00 ± 0.00 | 00.00 ± 0.00 | 00.00 ± 0.00 | 00.00 ± 0.00 |
| 03.12 | 100.00 ± 0.06 | 100.00 ± 0.02 | 100.00 ± 0.17 | 100.00 ± 0.03 |
| 06.25 | 100.00 ± 0.03 | 100.00 ± 0.08 | 99.00 ± 0.30 | 99.00 ± 0.70* |
| 12.50 | 100.00 ± 0.05 | 100.00 ± 0.02 | 99.00 ± 1.17 | 99.00 ± 0.08 |
| 25.00 | 65.00 ± 0.52 | 63.00 ± 3.09 | 80.00 ± 1.03 | 99.00 ± 2.56 |

TABLE 12

Protein entrapment stability of the system after three weeks of incubation at different temperatures

| Protein (mg) | Temperature | | | |
|---|---|---|---|---|
| | 4 C. | 25 C. | 37 C. | 60 C. |
| 00.00 | 00.00 ± 0.00 | 00.00 ± 0.00 | 00.00 ± 0.00 | 00.00 ± 0.00 |
| 03.12 | 100.00 ± 0.12 | 100.00 ± 0.10 | 100.00 ± 0.02 | 100.00 ± 0.06 |
| 06.25 | 100.00 ± 0.05 | 100.00 ± 0.08 | 100.00 ± 0.70 | 100.00 ± 0.03* |
| 12.50 | 100.00 ± 0.03 | 100.00 ± 0.05 | 100.00 ± 0.71 | 100.00 ± 0.47 |
| 25.00 | 66.00 ± 0.30 | 70.00 ± 1.46 | 76.00 ± 0.88 | 98.00 ± 0.47 |

*represents mean value ± SD, n = 3

The assay represented in Table 12 was conducted similarly as the one represented in Table 9, except that aliquots of adjuvant system mixed with different amount of BSA have been used.

Figure 11:
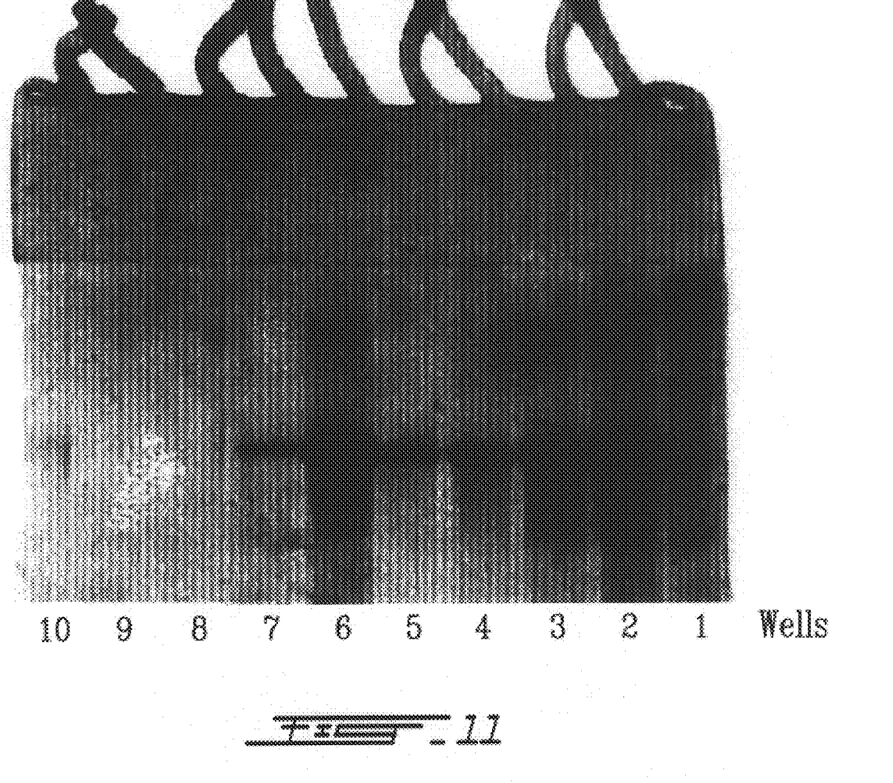
FIG. 11 represents a SDS-polyacrylamide gel showing the integrity of entrapped BSA after 2 years of storage of the system at 4° C.

The protein entrapped in the system of the present invention was still intact even after two years of storage as showed FIG. 11.

FIG. 11 illustrates the integrity of entrapped BSA after 2 years of storage of the system at 4° C. Here 10 μl of system suspensions initially mixed with different concentrations of BSA; 25.00, 12.5, 6.25, and 3.12 mg from the standard lane (Biorad high molecular weight standards) were diluted ½ in SDS sample buffer before being analyzed through a 12% SDS-PAGE gel after coomassie blue staining (lanes 6 to 9). The same corresponding amounts of free BSA (lanes 2 to 5) have been used as controls.

At low concentrations the protein was strongly entrapped in the system while at high concentrations, a portion of the protein amount was loosely entrapped in the system. The strongly entrapped protein did not enter into the gel. Only the loosely entrapped protein portion entered into the gel.

The results about the physico-chemical properties of the system of the present invention after 2 years of storage at 4 degrees in comparison to its freshly prepared counterpart clearly demonstrates that the system is a very stable delivery system with high capacity of entrapment of proteins even after two years of storage at 4° C. using BSA as protein model. The system did display neither a phase separation, creaming nor aggregation. The negatively charged organic emulsion was stabilized through its interactions with the positively charged inorganic phase.

The system readily entrapped any charged macromolecule by simple vortexing it with an equal volume of macromolecule solution as demonstrated BSA, influenza vaccine and DNA results. The facts that the system is stable for more than two years and was prepared from materials clinically approved using a well-accepted pharmaceutical procedure represent an great advantage in term of approbation by the FDA and the fulfillment of pharmaceutical requirements.

In the light of these results, It can be concluded that the system of the present invention is a very stable system with a high entrapment capacity on the sole basis of electrostatic charges.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A biphasic delivery system for charged molecules comprising a negatively charged hydrophobic organic phase and a positively charged inorganic phase, said organic phase and said inorganic phase being capable of entrapping charged molecules with electrostatic bonding of the charged molecules with the organic phase and the inorganic phase, wherein the organic phase is an oil-in-water emulsion comprising an electrostatically neutral oil and dicetylphosphate, and wherein the inorganic phase comprises alum.

2. The delivery system of claim 1, wherein the neutral oil is selected from the group consisting of squalane, soybean oil, sesame oil and peanut oil.

3. The delivery system of claim 1, wherein the delivery system has a diameter of at most five micrometers when said charged molecules are entrapped therein.

4. The delivery system of claim 1, further comprising charged molecules.

5. The delivery system of claim 4, wherein the charged molecules are DNA.

6. A method for producing a delivery system as defined in claim 1, said method comprising the steps of contacting a negatively charged hydrophobic organic phase with charged molecules and a positively charged inorganic phase and mixing same for entrapping said charged molecules between the organic phase and the inorganic phase, wherein the organic phase is an oil-in-water emulsion comprising an electrostatically neutral oil and dicetylphosphate, and wherein the inorganic phase comprises alum.

7. The method of claim 6, wherein the negatively charged organic phase and the charged molecules are first mixed together, followed by addition and mixing of the positively charged inorganic phase therein.

8. The method of claim 6, wherein the natural oil is selected from the group consisting of squalane, soybean oil, sesame oil and peanut oil.

9. The method of claim 6, wherein the delivery system has a diameter of a most five micrometers when said charged molecules are entrapped therein.

10. The method of claim 6, wherein said charged molecules are DNA.

* * * * *